(12) United States Patent
Busam et al.

(10) Patent No.: US 11,260,146 B2
(45) Date of Patent: Mar. 1, 2022

(54) SEAL-HEALING VALVE FOR A MEDICAL INSTRUMENT

(71) Applicant: Terumo Medical Corporation, Somerset, NJ (US)

(72) Inventors: Jonathan Busam, Kennett Square, PA (US); Kendra Gallagher, Wilmington, DE (US)

(73) Assignee: Terumo Medical Corporation, Somerset, NJ (US)

( * ) Notice: Subject to any disclaimer, the term of this patent is extended or adjusted under 35 U.S.C. 154(b) by 0 days.

(21) Appl. No.: 16/698,194

(22) Filed: Nov. 27, 2019

(65) Prior Publication Data

US 2021/0154361 A1  May 27, 2021

(51) Int. Cl.
*A61L 27/18* (2006.01)
*A61M 39/06* (2006.01)

(52) U.S. Cl.
CPC .............. *A61L 27/18* (2013.01); *A61M 39/06* (2013.01)

(58) Field of Classification Search
None
See application file for complete search history.

(56) References Cited

U.S. PATENT DOCUMENTS

| | | | |
|---|---|---|---|
| 4,610,665 A * | 9/1986 | Matsumoto | A61M 39/0606 604/167.04 |
| 4,610,674 A | 9/1986 | Suzuki et al. | |
| 4,673,393 A * | 6/1987 | Suzuki | A61M 39/0606 138/89 |
| 5,647,855 A | 7/1997 | Trooskin | |
| 5,738,664 A | 4/1998 | Erskine et al. | |
| 5,798,113 A | 8/1998 | Dionne et al. | |
| 6,566,406 B1 | 5/2003 | Pathak et al. | |
| 7,009,034 B2 | 3/2006 | Pathak et al. | |
| 8,401,633 B2 | 3/2013 | Hyde et al. | |
| 8,815,277 B2 | 8/2014 | Park et al. | |
| 9,006,364 B2 * | 4/2015 | Van Gemert | C08G 18/4277 526/260 |
| 9,259,473 B2 | 2/2016 | Messersmith et al. | |
| 9,603,997 B2 * | 3/2017 | Humayun | A61M 5/162 |
| 9,764,124 B2 | 9/2017 | Fallarida et al. | |
| 9,802,439 B2 | 10/2017 | Albenge et al. | |
| 10,177,326 B2 * | 1/2019 | Chung | C08G 77/388 |

(Continued)

FOREIGN PATENT DOCUMENTS

WO  2007127225 A2  11/2007
WO  2013123946 A1   8/2013

OTHER PUBLICATIONS

Van Gemert et al (Self-Healing Supramolecular Polymers in Action, Macromol. Chem. Phys. 2012, 213, pp. 234-242, Macromolecular Journals, Wiley-VCH Verlag GmbH & Co. KGaA, Weinheim).*

(Continued)

*Primary Examiner* — Tae H Yoon
(74) *Attorney, Agent, or Firm* — Quarles & Brady LLP; James J. Aquilina (57) ABSTRACT

The present application discloses medical instruments that utilize self-healing polymers as all or portion of the valves and valve assemblies thereof, such that these valves can self-heal while or after being punctured by an ancillary device during a surgical procedure and thereby help minimize blood loss and achieve hemostasis.

19 Claims, 8 Drawing Sheets

(56) References Cited

U.S. PATENT DOCUMENTS

| | | | |
|---|---|---|---|
| 10,238,851 B2 | | 3/2019 | Butziger et al. |
| 10,526,495 B2 | * | 1/2020 | Gao .................. C09D 5/00 |
| 2006/0142705 A1 | | 6/2006 | Halili |
| 2013/0053594 A1 | | 2/2013 | Lee et al. |
| 2015/0111987 A1 | | 4/2015 | Wilson |
| 2017/0008999 A1 | | 1/2017 | Odriozola et al. |
| 2017/0173273 A1 | | 6/2017 | Tallarida et al. |
| 2017/0182303 A1 | | 6/2017 | Tallarida et al. |
| 2020/0221928 A1 | * | 7/2020 | Rohl ................ A61B 1/00082 |

OTHER PUBLICATIONS

Lai, J.-C., et al., "Thermodynamically stable whilst kinetically labile coordination bonds lead to strong and tough self-healing polymers," Nature communications 10, Article No. 1164 (2019), Mar. 11, 2019, <URL: https://doi.org/10.1038/s41467-019-09130-z> (pp. 1-9).

Li, C.-H. et al., "Self-Healing Polymers Based on Coordination Bonds," Advanced Materials, vol. 32, No. 27, 1903762, First published: Oct. 10, 2019, <URL: https://doi.org/10.1002/ adma.201903762> (Abstract available only, 2 pages).

International Search Report from corresponding PCT Application No. PCT/US2020/060838, dated Mar. 10, 2021 (4 pages).

Written Opinion of the International Searching Authority from corresponding PCT Application No. PCT/US2020/060838, dated Mar. 10, 2021 (6 pages).

* cited by examiner

SEAL-HEALING VALVE FOR A MEDICAL INSTRUMENT

FIELD OF THE DISCLOSURE

The present disclosure relates to the use of self-healing valves and valve assemblies in medical instruments, and more particularly to the use of self-healing polymers as the material for puncture valves used in medical instruments employed during surgical applications.

BACKGROUND

The use of catheters, introducer sheaths, and other medical instruments to access vascular pathways is well known in the art. One known method of introducing a catheter into a blood vessel involves: first, puncturing the skin and the exterior wall of the blood vessel with a hollow needle to access the interior of the blood vessel; second, inserting a guidewire through the interior of the hollow needle into the interior of the blood vessel; third, removing the hollow needle so that the guidewire is left behind inside the blood vessel; fourth, using the guidewire to precisely insert an introducer sheath having a dilator into the interior of the blood vessel; and fifth, guiding the dilator and the catheter into the blood vessel until the catheter has reached its desired location. Various treatment or diagnostic devices can then be introduced into the blood vessel through the catheter.

During periods when a treatment device is inserted into a path of the main body of the catheter, it is desirable for the catheter to include a puncturable valve assembly in the path of the main body thereof, which conforms around the profile of the treatment device and thereby prevents both the introduction of air into the blood vessel and flow of the patient's blood to the exterior of the catheter. For the same reasons, it is also useful to have such a valve assembly in the main body of the introducer sheath during periods when the catheter is inserted within the introducer sheath. In the past, various elastomeric materials having various pre-cut hole geometries have been used for these valve assemblies. These valve assemblies are expensive and complicated to construct and will occasionally fail.

Accordingly, there is a need for a self-healing valve for a medical instrument that addresses these and other drawbacks of the prior art.

SUMMARY OF THE DISCLOSURE

In one respect, the present disclosure comprises a medical instrument, the medical instrument comprising: a main body having an axial path; at least one opening through which an ancillary device may be introduced into the main body along the axial path; and a valve assembly located adjacent to the opening along the axial path, the valve assembly comprising at least one material layer, the at least one material layer being at least partially comprised of a self-healing polymer that is capable of re-polymerization after being cut or punctured.

In another respect, the present disclosure comprises a valve assembly adapted for use in a medical instrument, the valve assembly comprising at least one material layer, the at least one material layer being at least partially comprised of a self-healing polymer that is capable of re-polymerization after being cut or punctured without the need for the inclusion of chemicals, catalysts, or plasticizers in the at least one material layer.

In yet another respect, the present disclosure comprises a method of constructing a medical instrument, the method comprising: forming a main body of the medical instrument with a path located interior thereto, the path having a hollow interior; forming an opening between an exterior of the medical instrument and the interior of the path; forming a valve assembly comprising at least one material layer that is at least partially comprised of a self-healing polymer that is capable of recovering its original shape after insertion of an ancillary medical device through the at least one material layer; and placing the valve assembly adjacent to the opening along the path.

BRIEF DESCRIPTION OF THE DRAWINGS

The present disclosure will hereinafter be described in conjunction with the appended drawing figures, wherein like numerals denote like elements.

DETAILED DESCRIPTION OF THE EMBODIMENT(S)

The ensuing detailed description provides exemplary embodiment(s) only, and is not intended to limit the scope, applicability, or configuration thereof. Rather, the ensuing detailed description of the exemplary embodiment(s) will provide those skilled in the art with an enabling description for implementing these embodiment(s). It should be understood that various changes may be made in the function and arrangement of elements of the embodiment(s) without departing from the spirit and scope of the invention, as set forth in the appended claims.

Directional terms (e.g., upper, lower, left, right, etc.) may be used herein. These directional terms are merely intended to assist in disclosing the embodiment(s) and claiming the invention and are not intended to limit the claimed invention in any way. In addition, reference numerals that are introduced in the specification in association with a drawing figure may be repeated in one or more subsequent figure(s) without additional description in the specification, in order to provide context for other features.

In the present specification and claims, unless stated otherwise, the terms "immediate" or "immediately" should be understood to have the definition of "within 10 seconds or less."

Various valve designs and geometries have been used in medical instruments that include puncture valves for insertion of catheters and various treatment devices (e.g., balloon catheters, stents, atherectomy devices, and endarterectory devices) therethrough during surgical procedures. Various catheter-introducing instruments and valve assemblies employing elastomeric materials are taught in, for example, U.S. Pat. Nos. 4,610,665, 4,610,674, and 4,673,393, the entire contents of each of which are hereby incorporated by reference.

Figure 2:
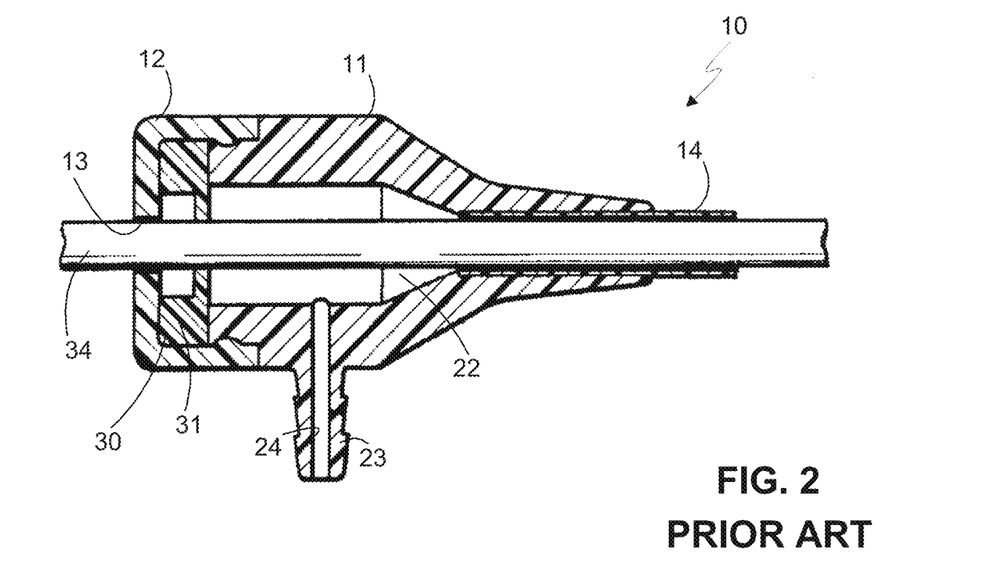
FIG. 2 is a sectional view of the prior art medical instrument of FIG. 1, with a dilator or other treatment device inserted through the valve assembly thereof.
Figure 3:
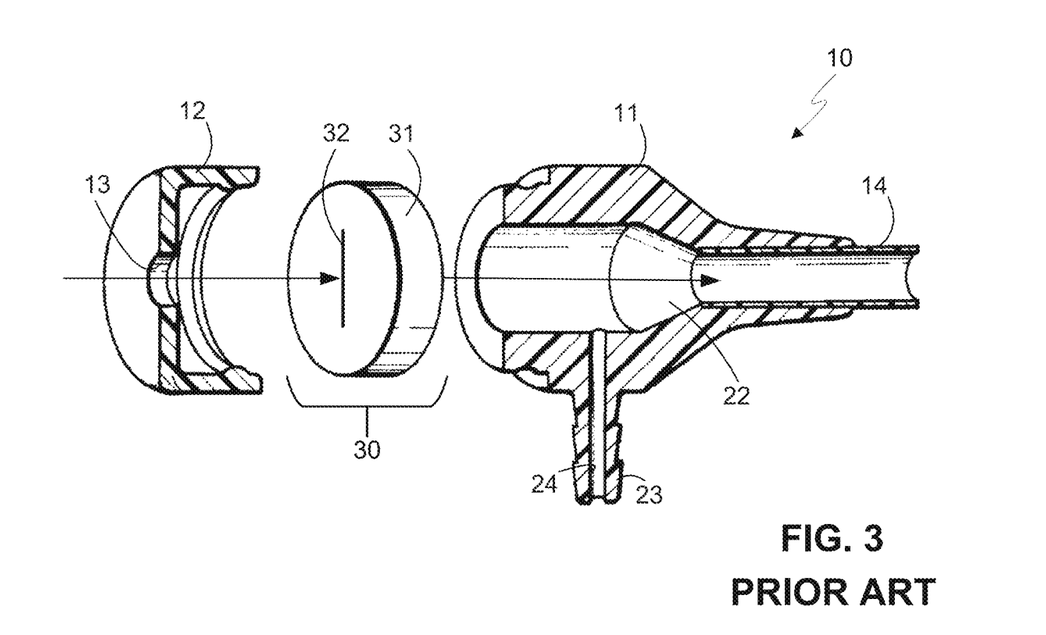
FIG. 3 is a perspective exploded view of the prior art medical instrument thereof, with the dilator or other treatment device removed from view.

As is known in the art, prior to introduction of a catheter or treatment device into a blood vessel to perform a procedure, a hollow needle is used to penetrate the epidermis and provide access to the blood vessel. A guidewire is then inserted through the central cavity of the hollow needle and into the interior of the blood vessel. The hollow needle is then removed, leaving the guidewire in place inside the blood vessel. Subsequently, a medical instrument, such as the catheter or sheath introducer 10 according to the prior art as shown in FIGS. 1-3, is used to introduce diagnostic or treatment devices into the blood vessel.

Figure 1:
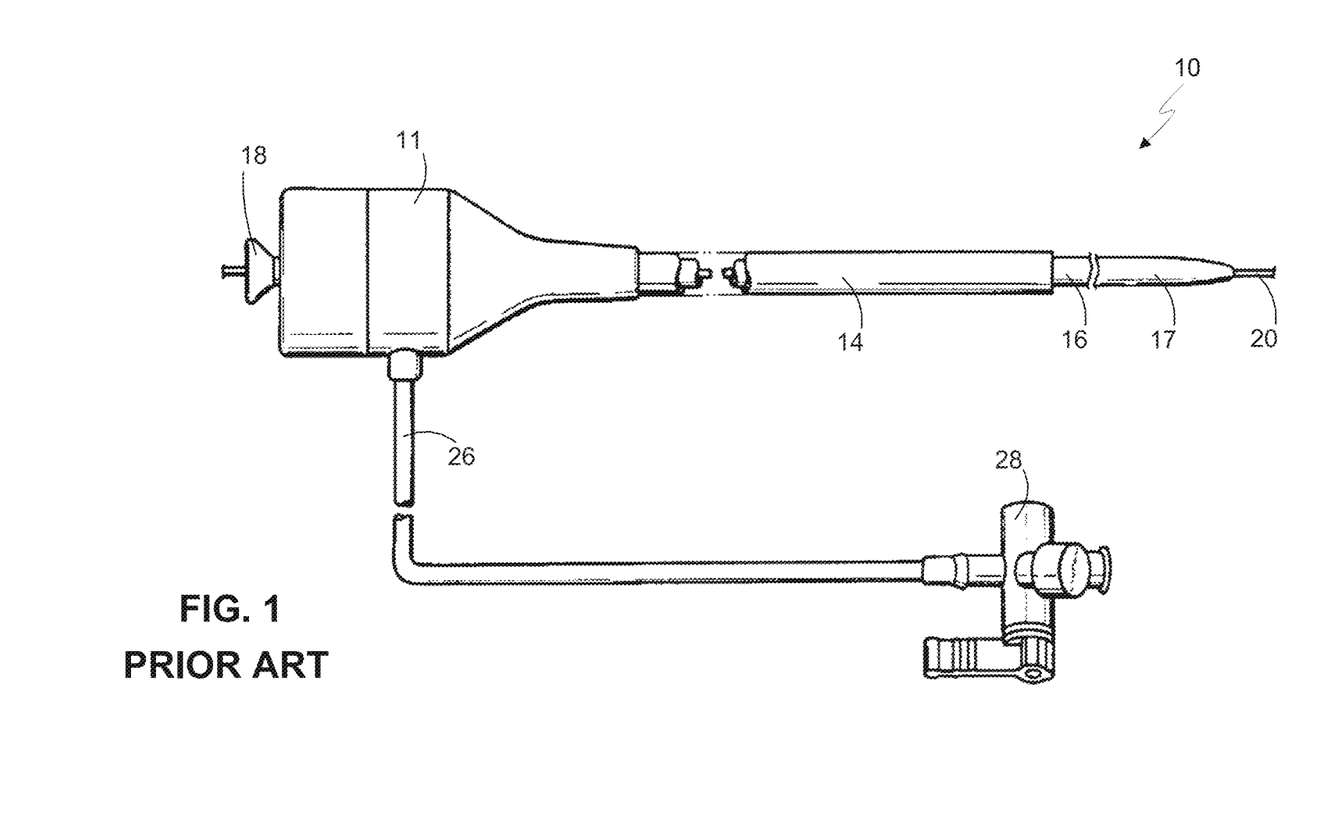
FIG. 1 is a side view of an exemplary medical instrument in the form of a catheter introducer according to the prior art, showing a state in which a guidewire and a dilator or other treatment device are inserted through the catheter introducer.

In the prior art device of FIG. 1, the medical instrument 10 is shown in a state in which a guidewire 20 and a dilator 16 are inserted through the catheter introducer 10. After the guidewire 20 has been left in place after removal of the hollow needle, a dilator 16, which has been inserted through an axial path 22 of the catheter introducer 10, surrounds and is coupled to the guidewire 20. The dilator 16 comprises a dilator hub 18 that is connectable with a main body (i.e., hub) 11 of the catheter introducer 10, and the forward end portion of the dilator tube 17 is insertable into the main body (i.e. hub) 11 and a flexible body 14 of the catheter introducer 10. Subsequent to the step of introducing the dilator 16 into the catheter introducer 10, the forward end portion of the dilator tube 17 of the dilator 16 is inserted through the wall of the affected blood vessel, and the flexible body 14 of the catheter introducer 10 is also introduced into the blood vessel, thus dilating the hole penetrating the blood vessel wall. In some instances, subsequent to this step, the guidewire 20 and dilator 16 are removed from the blood vessel while a fluid (e.g., an anti-coagulant or other fluid) is fed into the blood vessel via the axial path 22 of the catheter introducer 10 via a side tube 26 that is connected between a connecting portion 23 of the catheter introducer 10 and a three-way stopcock 28 to form a path 24 that is in fluid flow communication with the axial path 22 of the catheter introducer 10.

Figure 4:
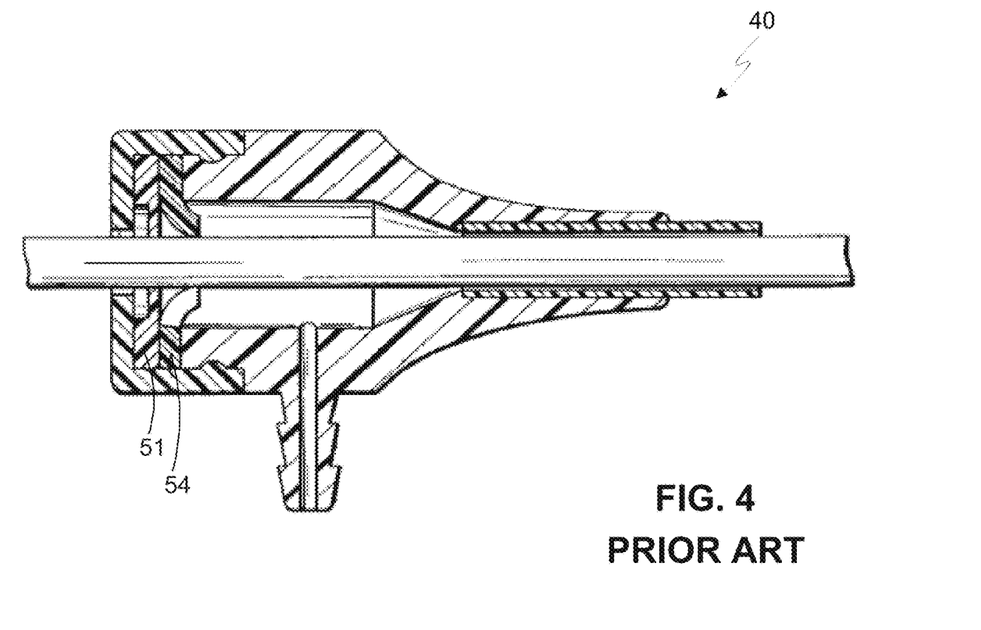
FIG. 4 is a sectional view of another medical instrument in the form of a catheter introducer according to the prior art, with a dilator or other treatment device inserted through the valve assembly thereof.
Figure 5:
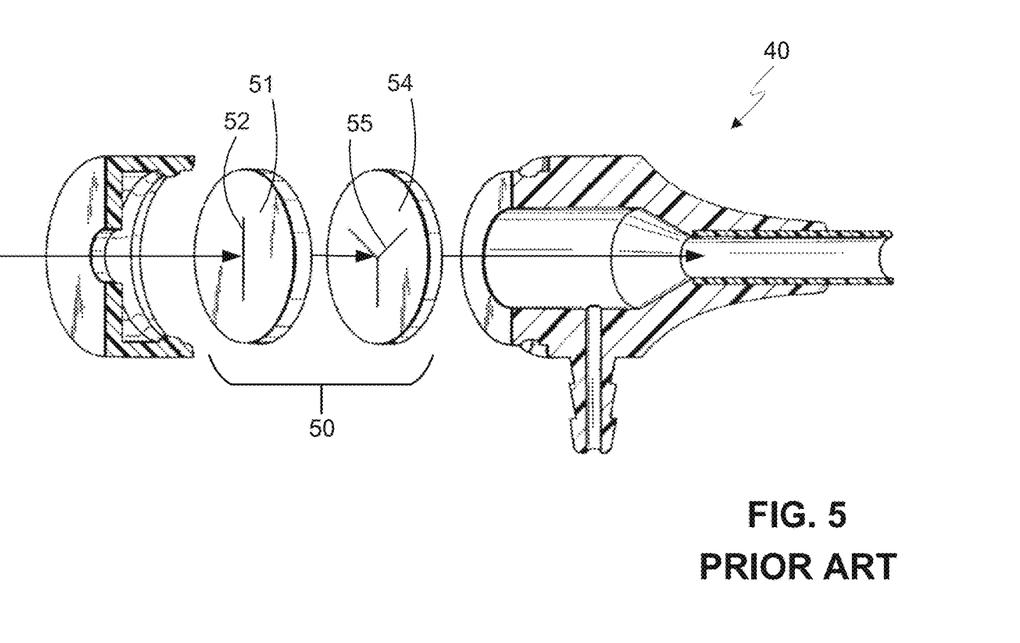
FIG. 5 is a perspective exploded view of the prior art medical instrument thereof, with the dilator or other treatment device removed from view.

While the guidewire 20 and the dilator 16 are inserted through the axial path 22 of the catheter introducer 10 as described above, a valve assembly 30 of the catheter introducer 10 secures and closes around the outer peripheral wall of the dilator 16 (or other treatment/diagnostic device that has been inserted through the valve assembly 30), so that blood outflow can be prevented. Subsequently, a catheter 34 is introduced through an opening 13 of a cap 12 of the catheter introducer 10 and penetrates through the valve assembly 30 thereof. As would be understood by those having ordinary skill in the art, the catheter 34 penetrates through the valve assembly 30, enters the main body 11 of the catheter introducer 10, is guided into the flexible sheath 14, and reaches the interior of the blood vessel. While the catheter 34 is inserted through the axial path 22 of the catheter introducer 10, the valve assembly 30 secures and closes around the outer peripheral wall of the catheter 34 (or other treatment/diagnostic device that has been inserted through the valve assembly 30), so that blood outflow can be prevented. Subsequently, when the catheter 34 is removed from the catheter introducer 10 and is no longer penetrating the valve assembly 30, the valve assembly 30 should be capable of avoiding blood outflow. In the prior art embodiment shown in FIGS. 1-3, the valve assembly 30 comprises a single valve 31 having intersecting slits (including slit 32) that are pre-cut through opposing faces of the valve 31. In the prior art embodiment of a catheter introducer 40 shown in FIGS. 4 and 5, the valve assembly 50 comprises a first valve 51 (including slit 52) and a second valve 54 (including radial slit 55). Except for their respective valve assemblies 30,50, these two prior art embodiments are otherwise identical in structure and function, and the construction of the embodiment of FIGS. 4 and 5 will not be discussed further. As explained in detail in U.S. Pat. Nos. 4,610,665, 4,610,674, and 4,673,393—which explain the prior art instrument and valve embodiments of FIGS. 1-3 and FIGS. 4-5 in detail—precise pre-cut slit geometries are used in the valve assemblies thereof to prevent blood outflow. However, as noted above, these prior art valves are expensive and complicated to manufacture and are occasionally prone to failure since they are comprised of elastomeric materials which do not re-polymerize, and therefore do not always provide a tight seal against the outer peripheral wall of the respective treatment device.

FIGS. 6-9 show various embodiments of sheath or catheter introducers according to the present disclosure, showing the use of one or more self-healing polymeric materials to form all or portions of the respective valve assembly. The assemblies shown in FIGS. 6-9 are exemplary only, and it should be understood that valve(s) that are all or partially comprised of self-healing polymeric materials could be used in such medical instruments in various additional configurations, in combination with or in the absence of previously-known valve designs and materials, without departing from the scope and spirit of the present disclosure. Due to their ability to quickly provide a tight seal against the outer peripheral wall thereof, the use of self-healing polymeric materials as the material that comprises all or part of a valve assembly used in a vascular access device (e.g., sheath or catheter introducers and treatment or diagnostic devices such as balloon catheters, stents, atherectomy devices, and endarterectory devices) permits the introduction of these various medical devices through the introducer or catheter while both preventing blood leakage from the blood vessel and preventing the introduction of air into the blood vessel. While FIGS. 6-9 show the use of valve assemblies comprising self-healing polymeric materials in exemplary sheath or catheter introducers, one having ordinary skill in the art would understand that this same category of materials could be used within catheters and other vascular access instruments, without departing from the scope of the present disclosure.

Figure 6:
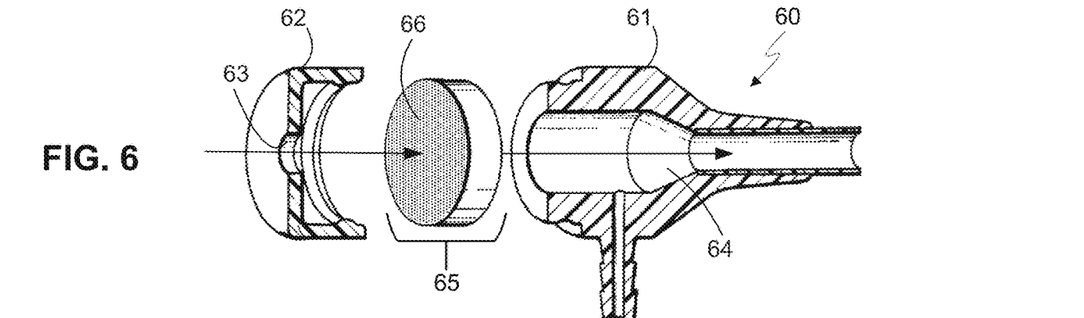
FIG. 6 is an embodiment of a medical instrument in the form of a catheter introducer according to the present disclosure, showing the use of a valve assembly comprising a self-healing polymeric material.
Figure 7:
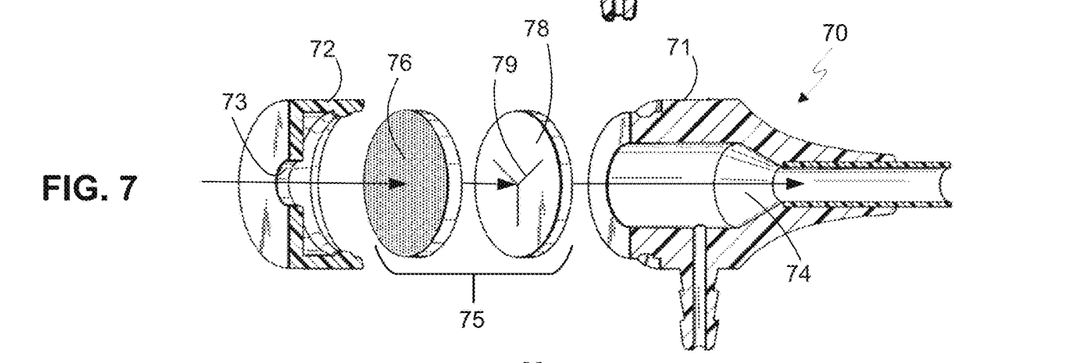
FIG. 7 is another embodiment of a medical instrument in the form of a catheter introducer according to the present disclosure, showing the use of a valve assembly comprising a self-healing polymeric material.
Figure 8:
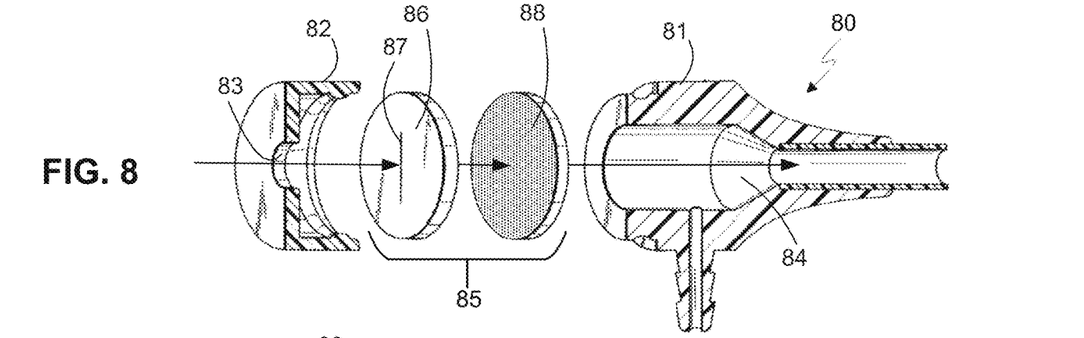
FIG. 8 is another embodiment of a medical instrument in the form of a catheter introducer according to the present disclosure, showing the use of a valve assembly comprising a self-healing polymeric material.
Figure 9:
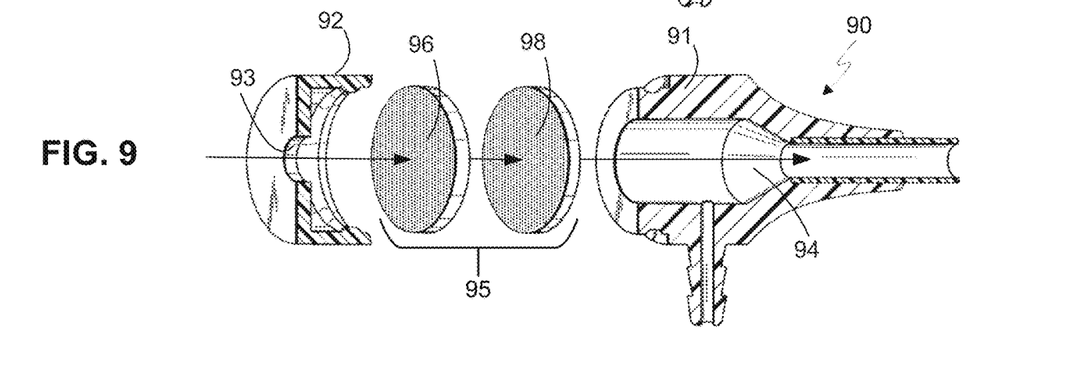
FIG. 9 is another embodiment of a medical instrument in the form of a catheter introducer according to the present disclosure, showing the use of a valve assembly comprising a self-healing polymeric material.

The sheath or catheter introducer 60 of FIG. 6 comprises a main body 61 having an axial path 64 through which ancillary medical device(s) may be inserted, a cap 62 having an opening 63 to accommodate insertion of the ancillary medical device(s), and a valve assembly 65 comprising a single valve 66 comprised of a self-healing polymeric material according to the present disclosure. In this embodiment, the single valve 66 of the valve assembly 65 is fitted within the cap 62 and secured in place between the cap 62 and the main body 61 of the sheath or catheter introducer 60. The sheath or catheter introducer 70 of FIG. 7 comprises a main body 71 having an axial path 74 through which ancillary medical device(s) may be inserted, a cap 72 having an opening 73 to accommodate insertion of the ancillary medical device(s), and a valve assembly 75 comprising a first valve 76 comprised of a self-healing polymeric material according to the present disclosure and a second valve 78 having a radial slit 79 in accordance with previously-known valve designs. In this embodiment, the first valve 76 and second valve 78 of the valve assembly 75 are sandwiched together, fitted within the cap 72, and secured in place between the cap 72 and the main body 71 of the sheath or catheter introducer 70. The sheath or catheter introducer 80 of FIG. 8 comprises a main body 81 having an axial path 84 through which ancillary medical device(s) may be inserted, a cap 82 having an opening 83 to accommodate insertion of the ancillary medical device(s), and a valve assembly 85 comprising a first valve 86 having a slit 87 in accordance with previously-known valve designs and a second valve 88 comprised of a self-healing polymeric material according to the present disclosure. In this embodiment, the first valve 86 and second valve 88 of the valve assembly 85 are sandwiched together, fitted within the cap 82, and secured in place between the cap 82 and the main body 81 of the sheath or catheter introducer 80. The sheath or catheter introducer 90 of FIG. 9 comprises a main body 91 having an axial path 94 through which ancillary medical device(s) may be inserted, a cap 92 having an opening 93 to accommodate insertion of the ancillary medical device(s), and a valve assembly 95 comprising a first valve 96 and a second valve 98, both of which are comprised of a self-healing polymeric materials according to the present disclosure. In this embodiment, the first valve 96 and second valve 98 of the valve assembly 95 are sandwiched together, fitted within the cap 92, and secured in place between the cap 92 and the main body 91 of the sheath or catheter introducer 90. Although not labeled in the Figures, each of the embodiments shown in FIGS. 6-9 includes a respective secondary path that is in fluid flow communication with the respective axial paths 64,74,84,94.

Any of the instruments taught in any of the prior art references noted above could be modified to include valve assemblies that incorporate one or more of the self-healing polymeric materials according to the present disclosure, and any of the valve assemblies taught in any of these references could be used—with appropriate modifications having been made, as would be appreciated by a person having ordinary skill in the art—in any known or hereafter-invented introducer sheath, catheter, or other medical instrument used to provide access to a blood vessel having puncturable valves or other hemostasis valves, by incorporating one or more of the self-healing polymeric materials according to the present disclosure.

Using self-healing polymer(s) to form all or portion(s) of a medical instrument's hemostasis valve would permit it to seal itself around the profile of ancillary devices of various profiles and dimensions during a medical procedure, thus reducing or eliminating instances of valve leakage in the form of blood loss. Such sealing around the profile of an ancillary medical device occurs through dynamic imine interactions or reversible intra- and inter-molecular ligand exchange processes over some desirable period of time (e.g., 15 minutes or less, 5 minutes or less, 3 minutes or less, 2 minutes or less, 60 seconds or less, 30 seconds or less, 15 seconds or less, 10 seconds or less, or 5 seconds or less) from introduction of the ancillary device through the valve assembly. In addition, after removal of the ancillary device from the valve assembly of the medical instrument, the autonomous self-healable elastomers used in the medical instruments according to the present disclosure are capable of complete, autonomous self-healing (i.e., re-sealing of the valve assembly) through dynamic imine interactions or reversible intra- and inter-molecular ligand exchange processes over some desirable period of time (e.g., 15 minutes or less, 5 minutes or less, 3 minutes or less, 2 minutes or less, 60 seconds or less, 30 seconds or less, 15 seconds or less, 10 seconds or less, or 5 seconds or less from removal of any ancillary device from the puncture), preferably but optionally without the need for the inclusion of chemicals, catalysts, or plasticizers in the valve material, and preferably but optionally under standard temperature and pressure (STP) conditions. The selected materials may be used in valves having any possible dimensions, but are preferably at least suitable for use in valves having a thickness in the range of 0.1 mm-10 mm to accommodate ancillary devices (e.g., catheters) ranging between 1 Fr-30 Fr (i.e., 0.33 mm to 10 mm). Further, the polymeric materials used for the autonomous self-healing valves could also meet certain characteristics or established standards with respect to biocompatibility and/or grade quality, e.g., meet certain standards for biocompatibility and/or for qualification as "medical grade" materials suitable for use in a hospital or surgical setting.

The inventors have identified various polymers that would be suitable as the self-healing material(s) used for the valve assemblies according to the present disclosure. These polymers include, but are not limited to, several materials having primarily polydimethylsiloxane (PDMS) and polyurethane (PUR) backbones. One such suitable self-healing material is sold by SupraPolix B.V. of Eindhoven, The Netherlands, and includes reversible hydrogen bonds. This material is available in multiple forms, including compounds that include: (1) associations of diacids and triacids from renewable resources; (2) triple-Hydrogen-bonds formed between thymine (Thy) and 2,6-diaminotriaine (DAT); (3) dimerization of ureidopyrimidinone (UPy) units by quadruple-Hydrogen bonds (H-bonds); and (4) copolymers combining hard polystyrene (PS) backbones with soft polyacrylate amide (PAA) pendant groups carrying multiple H-bonds.

Other suitable polymers include two substrates having different length PDMS chains, as identified below:

(1) BTA-PDMS-25000 (length=25000), in which a PDMS elastomer is formed by crosslinking long chains of bis(3-aminopropyl)-terminated PDMS with a tetra-functional biphenyl unit via an aldimine polycondensation reaction; and (2) Zn(Hbimcp)$_2$-PDMS (length=700-900), wherein (Hbimcp=2,6-bis((imino)methyl)-4-chlorophenol).

Other self-healing polymers capable of re-polymerization may also be suitable as the valve material, in accordance with the present disclosure.

Figure 10:
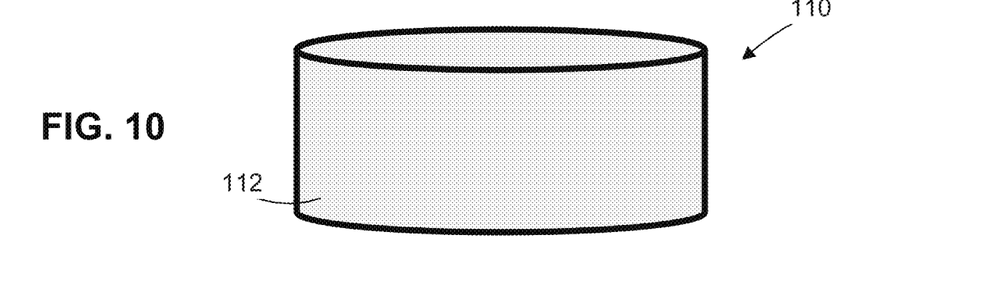
FIG. 10 is a schematic diagram of an embodiment of a valve assembly comprising a self-healing polymeric material, according to the present disclosure.
Figure 11:
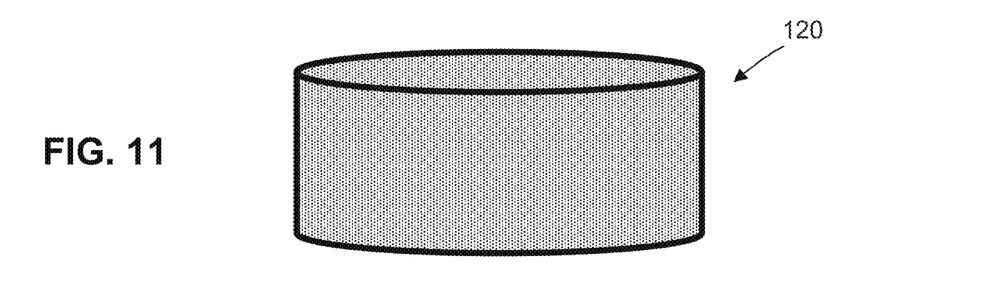
FIG. 11 is a schematic diagram of another embodiment of a valve assembly comprising a self-healing polymeric material, according to the present disclosure.
Figure 12:
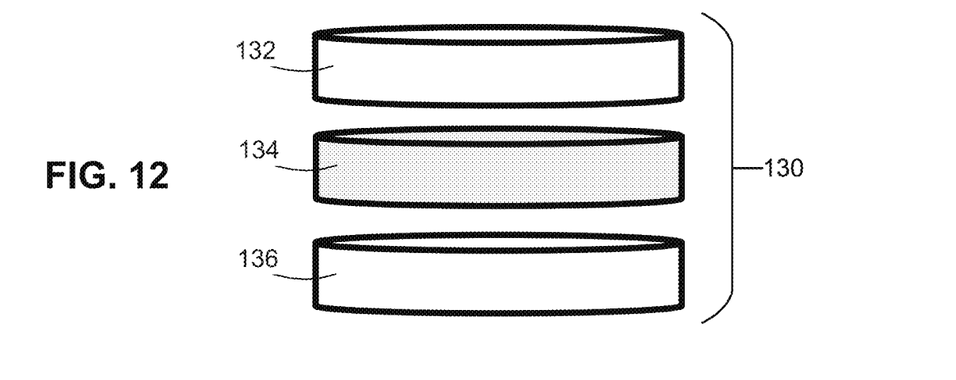
FIG. 12 is a schematic diagram of another embodiment of a valve assembly comprising a self-healing polymeric material, according to the present disclosure.
Figure 13:
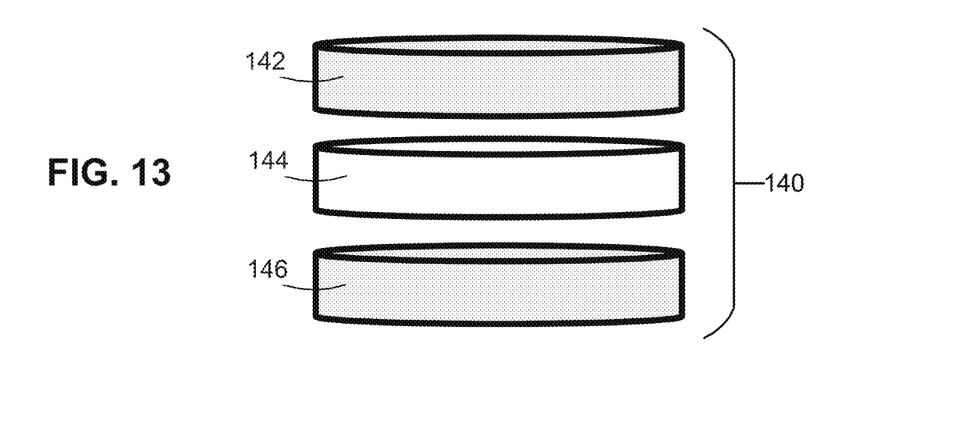
FIG. 13 is a schematic diagram of another embodiment of a valve assembly comprising a self-healing polymeric material, according to the present disclosure.

The self-healing polymeric materials according to the present disclosure could be integrated either fully or partially into the one or more valve(s) in various ways. In some embodiments, as shown schematically in FIG. 10, a valve assembly 110 according to the present disclosure comprises a uniform construction of a self-healing polymer as a single layer 112. In alternative embodiments, as shown schematically in FIG. 11, a valve assembly 120 according to the present disclosure comprises a uniform construction of a self-healing polymer that has been microencapsulated and mixed into a PDMS or PUR material. In any of the envisioned embodiments, the self-healing polymer could be activated based on hydrogen bonds or microencapsulation. In further alternative embodiments, as shown schematically in FIG. 12, a valve assembly 130 according to the present disclosure could comprise multiple layer(s) 132,136 of PDMS or PUR surrounding one or more layer(s) 134 of the self-healing polymeric material, which may be either of uniform construction or microencapsulated into a PDMS or PUR material. In yet further alternative embodiments, as shown schematically in FIG. 13, a valve assembly 140 according to the present disclosure could comprise multiple layer(s) of the self-healing polymeric material 142,146—which may be of uniform construction or microencapsulated into a PDMS or PUR material—surrounding one or more layer(s) 144 of PDMS or PUR.

FIGS. 14A-16D photographically show various methods of cutting or puncturing various self-healing polymeric materials and testing their self-healing characteristics. It should be clearly understood that all of these polymeric materials would be suitable to form all or part of a valve assembly for the various medical instruments described herein, in any of the configurations or forms described herein or in other configurations or forms as would be understood by a person having ordinary skill in the art, as described above in detail.

Figures 14A, 14B:
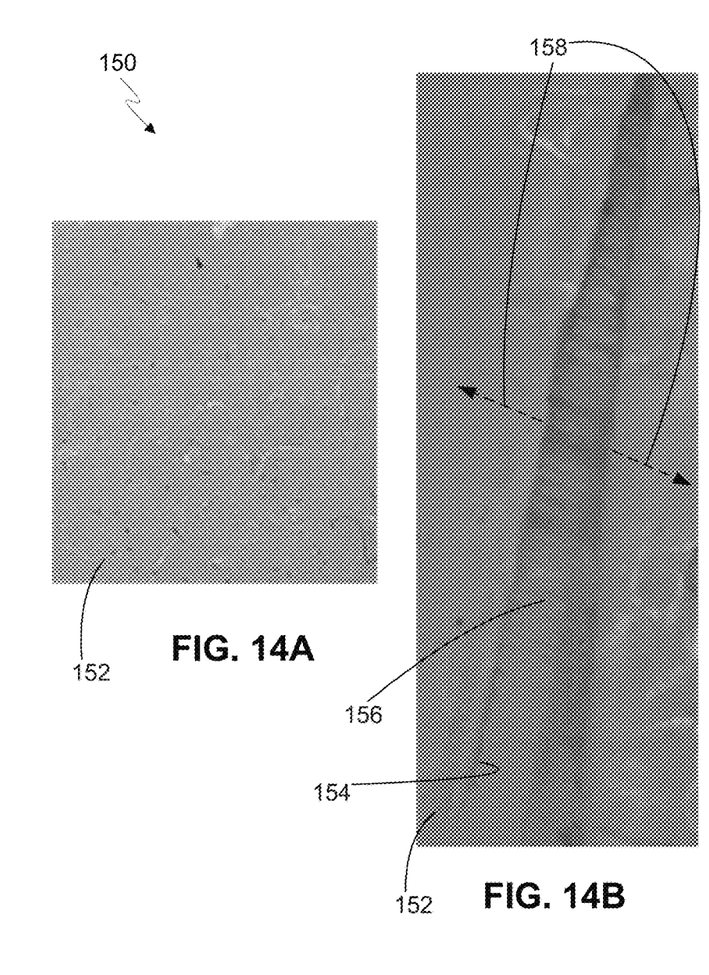
FIGS. 14A-14D show various steps of a method of cutting a first self-healing polymeric material and testing its self-healing characteristics.
Figure 14C:
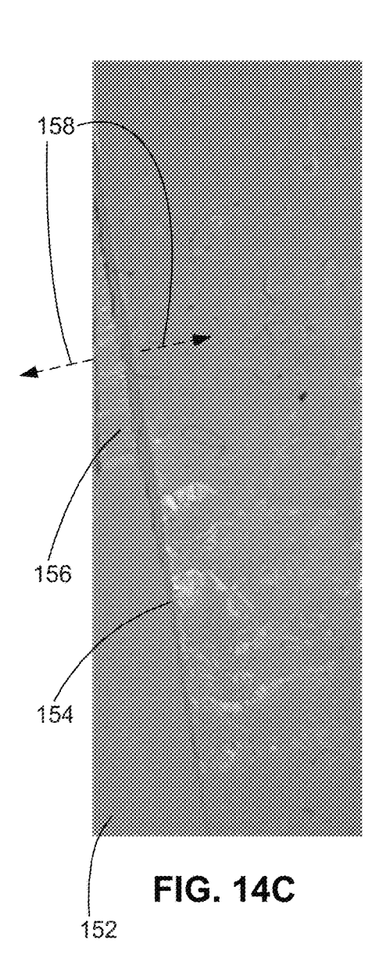
Figure 14D:
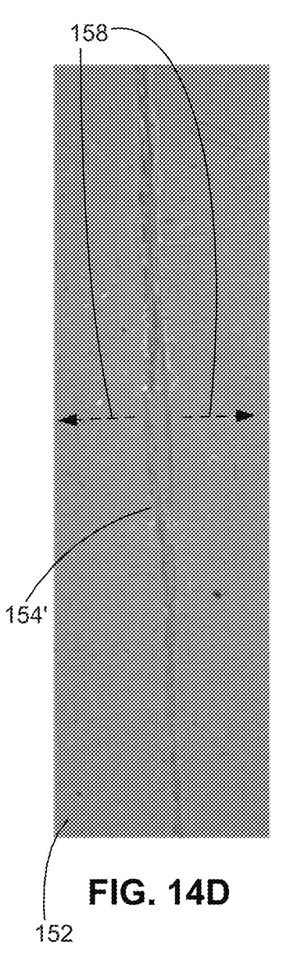

FIGS. 14A-14D show a method 150 of testing the self-healing characteristics of a material layer 152 of SupraPolix B.V.'s polymeric material having reversible Hydrogen bonds. In FIG. 14A, the material layer 152 is shown at 30× magnification prior to being cut. In FIG. 14A, the material layer 152 has no visible damage but shows slight imperfections in its surface. FIGS. 14B and 14C show the material layer 152 at 30× magnification 30 seconds after a cut 154 has been made all the way through the thickness of the material layer 152, and while the material layer 152 is being pulled in opposing tension directions 158 which are approximately orthogonal to the axial direction of the cut 154. During this period of healing, material adhesions 156 are visible while the cut 154 is in tension, showing the autonomous self-healing process via activation of hydrogen bonds of the material layer 152. FIG. 14D shows the material layer 152 at 30× magnification 60 seconds after the cut 154 was made through the thickness of the material layer 152, while the material layer 152 is being pulled in the tension directions 158. At this point, some small adhesions (not labeled) are still visible, but the cut 154 has now largely healed (e.g., where designated by reference numeral 154' in FIG. 14D).

Figure 15A:
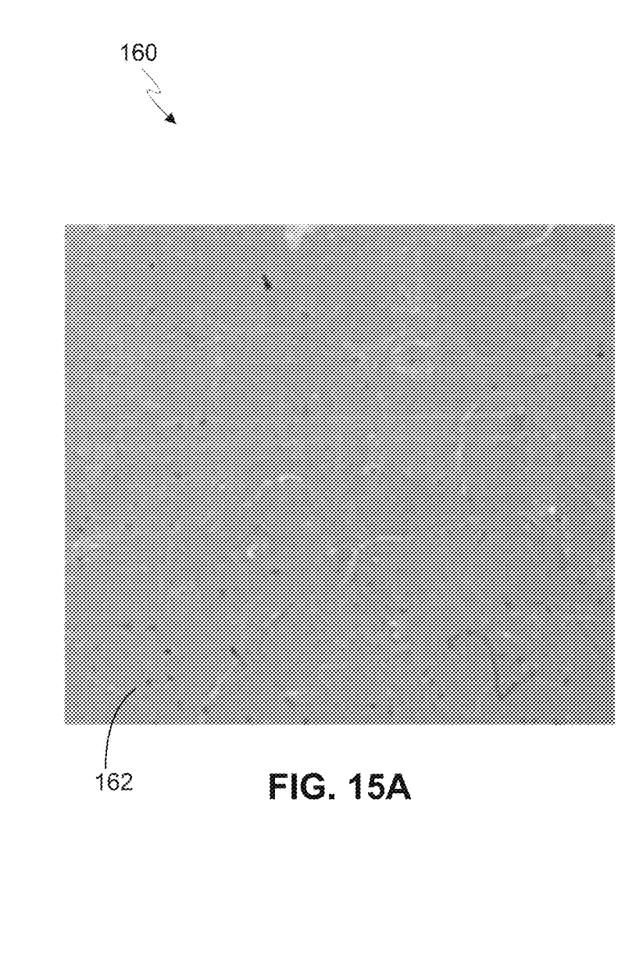
FIGS. 15A-15C show various steps of a method of cutting a second self-healing polymeric material and testing its self-healing characteristics.
Figure 15B:
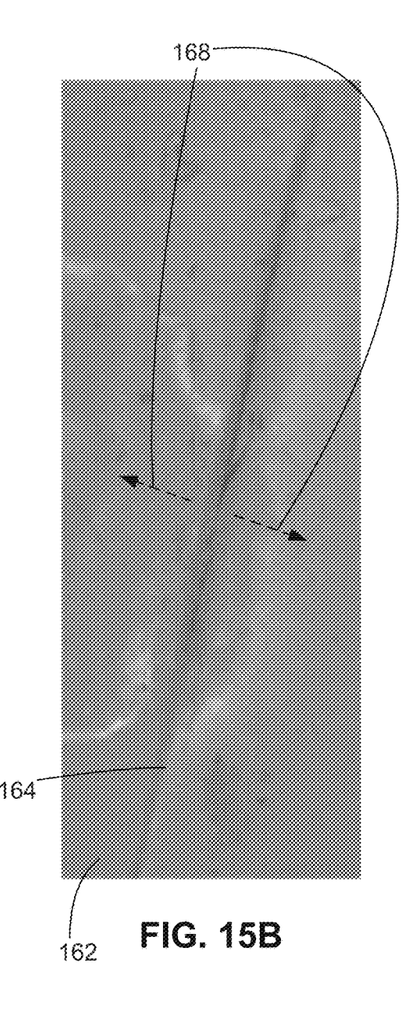
Figure 15C:
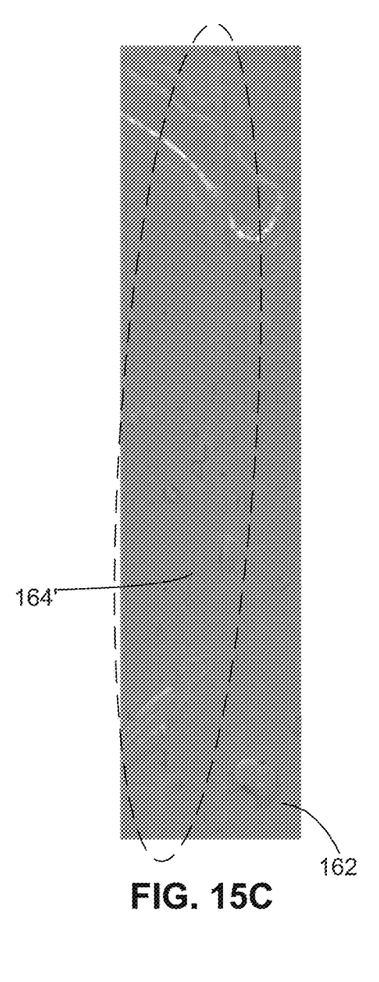

FIGS. 15A-15C show a method 160 of testing the self-healing characteristics of another material layer 162 of SupraPolix B.V.'s polymeric material having reversible Hydrogen bonds. In FIG. 15A, the material layer 162 is shown at 30× magnification prior to being cut. In FIG. 15A, the material layer 162 has no visible damage but shows slight imperfections in its surface. FIG. 15B shows the material layer 162 at 30× magnification immediately after a cut 164 has been made all the way through the thickness of the material layer 162, in the absence of tension. FIG. 15C shows the material layer 162 at 30× magnification 60 seconds after the cut 164 was made through the thickness of the material layer 162, while the material layer 162 is being pulled in opposing tension directions 168 which are approximately orthogonal to the axial direction of the cut 164. At this point, a minimal scar is still observable in the material layer 162 (see area generally enclosed by an oval), but the cut 164 did not separate under tension. The healed cut is designated by reference numeral 164' in FIG. 15C.

Figure 16A:
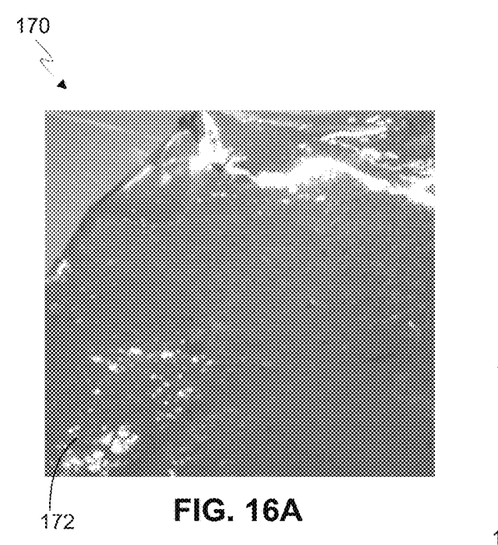
FIGS. 16A-16D show various steps of a method of cutting and puncturing a third self-healing polymeric material and testing its self-healing characteristics.
Figure 16B:
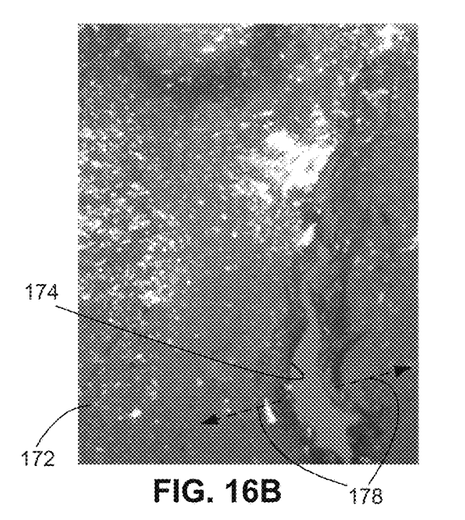
Figure 16C:
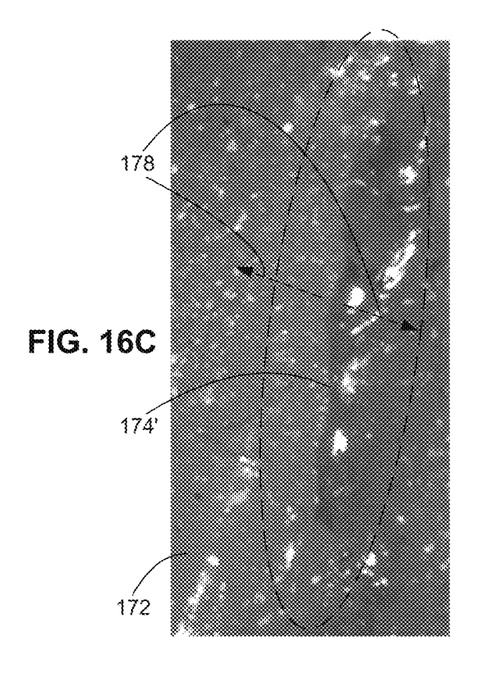
Figure 16D:
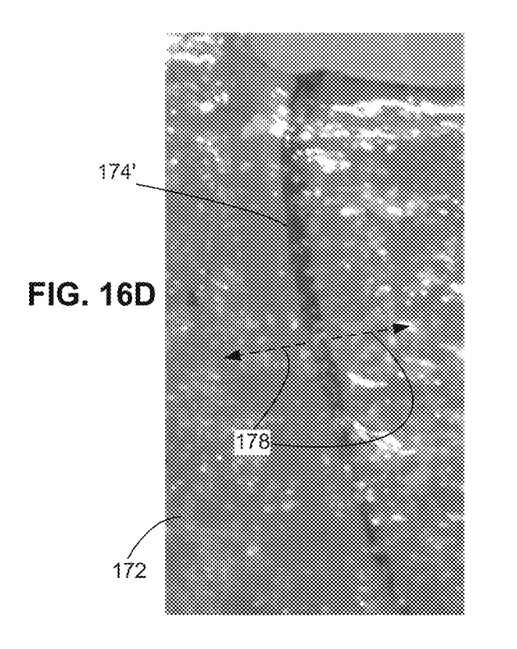

FIGS. 16A-16D show a method 170 of testing the self-healing characteristics of a material layer 172 of the BTA-PDMS-25000 polymeric material noted above. In FIG. 16A, the material layer 172 is shown at 50× magnification prior to being cut. In FIG. 16A, the material layer 172 has no visible damage but shows slight imperfections in its surface. FIG. 16B shows the material layer 172 at 50× magnification immediately after a cut 174 has been made all the way through the thickness of the material layer 172, while the material layer 172 is being pulled in opposing tension directions 178 which are approximately orthogonal to the axial direction of the cut 174. FIGS. 16C and 16D show the material layer 172 at 100× magnification 60 seconds after the cut 174 was made through the thickness of the material layer 172, while being pulled in tension in opposing tension directions 178. At this point, a minimal scar is still observable in the material layer 172 (see area generally enclosed by an oval in FIG. 16C), but the cut 174 did not separate under tension. The healed cut is designated by reference numeral 174' in FIGS. 16C and 16D.

While the principles of the claimed invention have been described above in connection with specific embodiment(s), it is to be clearly understood that this description is made only by way of example and not as a limitation of the scope of the invention, as set forth in the appended claims.

The invention claimed is:

1. A medical instrument, the medical instrument comprising:
  a main body having an axial path;
  at least one opening through which an ancillary device may be introduced into the main body along the axial path; and
  a valve assembly located adjacent to the opening along the axial path, the valve assembly comprising at least one material layer, the at least one material layer being at least partially comprised of a self-healing polymer that is capable of re-polymerization after being cut or punctured, wherein the at least one material layer comprises the self-healing polymer in microencapsulated form mixed with polydimethylsiloxane (PDMS) or polyurethane (PUR).

2. The medical instrument of claim 1, wherein the at least one material layer is capable of re-polymerization after being cut or punctured without the need for the inclusion of chemicals, catalysts, or plasticizers in the valve assembly.

3. The medical instrument of claim 1, wherein the at least one material layer is capable of completely recovering its original shape at standard temperature and pressure (STP) conditions within three minutes after being cut or punctured.

4. The medical instrument of claim 1, wherein the self-healing polymer has a polydimethylsiloxane (PDMS) backbone.

5. The medical instrument of claim 1, wherein the self-healing polymer has a polyurethane (PUR) backbone.

6. The medical instrument of claim 1, wherein the self-healing polymer comprises a PDMS elastomer formed by crosslinking chains of bis(3-aminopropyl)-terminated PDMS with a tetra-functional biphenyl unit via an aldimine polycondensation reaction.

7. The medical instrument of claim 6, wherein the self-healing polymer has a main backbone of length 25000.

8. The medical instrument of claim 1, wherein the self-healing polymer comprises $Zn(Hbimcp)_2$-PDMS, wherein (Hbimcp=2,6-bis((imino)methyl)-4-chlorophenol).

9. The medical instrument of claim 8, wherein the self-healing polymer has a main backbone of a length between 700-900.

10. The medical instrument of claim 1, wherein the valve assembly comprises a plurality of material layers.

11. The medical instrument of claim 10, wherein the valve assembly comprises at least one material layer that is at least partially comprised of the self-healing polymer that is capable of re-polymerization after being cut or punctured, located between additional material layers comprised of PDMS or PUR in the absence of said self-healing polymer.

12. The medical instrument of claim 1, the medical instrument further comprising a flexible sheath aligned with the axial path, the flexible sheath having a second opening opposite the at least one opening.

13. The medical instrument of claim 1, the medical instrument further comprising a cap attached to the main body, wherein the at least one opening is located in the cap.

14. The medical instrument of claim 1, the medical instrument further comprising a connecting portion adapted for attachment of a side tube thereto, the connecting portion having a path that is in fluid flow communication with the axial path of the main body.

15. A valve assembly adapted for use in a medical instrument, the valve assembly comprising at least one material layer, the at least one material layer being at least partially comprised of a self-healing polymer that is capable of re-polymerization after being cut or punctured without the need for the inclusion of chemicals, catalysts, or plasticizers in the at least one material layer, wherein the at least one material layer comprises the self-healing polymer in microencapsulated form mixed with polydimethylsiloxane (PDMS) or polyurethane (PUR).

16. The valve assembly of claim 15, wherein the at least one material layer is capable of completely recovering its original shape at standard temperature and pressure (STP) conditions within three minutes after being cut or punctured.

17. The valve assembly of claim 15, wherein the self-healing polymer has a polydimethylsiloxane (PDMS) backbone.

18. A method of constructing a medical instrument, the method comprising:
   forming a main body of the medical instrument with a path located interior thereto, the path having a hollow interior;
   forming an opening between an exterior of the medical instrument and the interior of the path;
   forming a valve assembly comprising at least one material layer that is at least partially comprised of a self-healing polymer that is capable of recovering its original shape after insertion of an ancillary medical device through the at least one material layer, the at least one material layer comprising the self-healing polymer in microencapsulated form mixed with polydimethylsiloxane (PDMS) or polyurethane (PUR); and
   placing the valve assembly adjacent to the opening along the path.

19. The method of claim 18, wherein the step of forming the valve assembly further comprises forming the at least one material layer of the self-healing polymer, the self-healing polymer being capable of completely recovering its original shape at standard temperature and pressure (STP) conditions within three minutes after being cut or punctured.

* * * * *